United States Patent [19]

Page

[11] Patent Number: 5,202,435
[45] Date of Patent: Apr. 13, 1993

[54] PROCESS FOR THE PREPARATION OF MORICIZINE HYDROCHLORIDE

[75] Inventor: Gary O. Page, Newark, Del.

[73] Assignee: Du Pont Merck Pharmaceutical Company, Wilmington, Del.

[21] Appl. No.: 789,487

[22] Filed: Nov. 12, 1991

[51] Int. Cl.$^5$ .......................................... C07D 279/30
[52] U.S. Cl. ........................................................ 544/39
[58] Field of Search ........................................... 544/39

[56] References Cited

U.S. PATENT DOCUMENTS 3,740,395  6/1973  Gritsenko et al. .................. 544/39
3,864,487  2/1975  Gritsenko et al. .................. 540/39

FOREIGN PATENT DOCUMENTS 332835    2/1979  U.S.S.R. ............................. 544/39
1269969   4/1972  United Kingdom .

OTHER PUBLICATIONS

Makharadze, et al., *Khim. Farm. Zh.*, 1988, 22, 732 and English translation.
Gritsenko, et al., English translation *Khim. Farm. Zh.*, 1972, 17-19.

*Primary Examiner*—Mark L. Berch
*Attorney, Agent, or Firm*—Gildo E. Fato; Joe Lucci; Blair Q. Ferguson

[57] ABSTRACT

Processes are provided for preparing crystalline moricizine hydrochloride from moricizine using hydrochloric acid, wherein the crystalline moricizine hydrochloride so obtained is substantially free of occluded water.

15 Claims, No Drawings

PROCESS FOR THE PREPARATION OF MORICIZINE HYDROCHLORIDE

FIELD OF THE INVENTION

This invention relates to processes for preparing crystalline moricizine in ethanol hydrochloride from moricizine using hydrochloric acid, wherein the crystalline moricizine hydrochloride so obtained is substantially free of occluded water.

BACKGROUND OF THE INVENTION

Pharmaceutical compositions comprising moricizine hydrochloride (10-(3-morpholinopropionyl)-phenothiazine-2-carbamic acid ethyl ester hydrochloride; Formula I) as an active ingredient are known to possess utility in the treatment of heart arrhythmia. For example, U.S. Pat. Nos. 3,740,395 and 3,864,487, in the names of Gritsenko, et al., indicate that moricizine hydrochloride is superior to other antiarrhythmic drugs such as quinidine and novocainamide in that it exhibits a broader spectrum of therapeutic action and is devoid of toxic side effects.

Ethmozine® brand of moricizine hydrochloride is marketed by The Dupont Merck Pharmaceutical Company, Wilmington, DE for the treatment of heart arrhythmia.

The structure of moricizine hydrochloride is shown below:

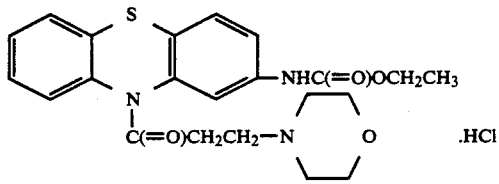

Typically, moricizine hydrochloride has been synthesized by processes in which moricizine free base (10-(3-morpholinopropionyl)-phenothiazine-2-carbamic acid ethyl ester) is contacted with hydrogen chloride gas in anhydrous organic solvents such as toluene or diethyl ether. Such processes, however, are inherently hazardous due to their employment of gaseous hydrogen chloride and, further, are difficult to control.

Accordingly, there exists a need in the art for synthetic routes to moricizine hydrochloride that do not employ gaseous hydrogen chloride.

SUMMARY OF THE INVENTION

The present invention provides synthetic processes wherein hydrochloric acid, that is , an aqueous solution of hydrogen chloride, is used instead of gaseous hydrogen chloride to convert moricizine free base to moricizine hydrochloride under carefully controlled reaction conditions. Moricizine free base is referred to herein as moricizine. The processes of the present invention comprise contacting a first solution of moricizine and a water-miscible organic solvent with hydrochloric acid to produce a second solution comprising moricizine hydrochloride, and then isolating the moricizine hydrochloride from the second solution. It has been discovered in accordance with the invention that substantially non-hydrated moricizine hydrochloride, substantially free of occluded water, can be isolated from the second solution by optimizing at least one of four identified reaction conditions: (1) the mole ratio of solvent to moricizine used; (2) the mole ratio of acid to moricizine used; (3) the amount of water introduced by the acid; or (4) the rate at which the moricizine hydrochloride is allowed to crystallize from the second solution. In preferred embodiments, all four reaction conditions are optimized as follows: the first solution comprises at least about 30 equivalents ethanol per equivalent moricizine; the hydrochloric acid comprises about 36.5 weight percent hydrogen chloride and at least about 1 equivalent hydrogen chloride per equivalent moricizine; and the isolating step comprises crystallizing moricizine hydrochloride from the second solution at a relatively slow rate to produce crystalline moricizine hydrochloride which is substantially non-hydrated, that is, substantially free of occluded water.

DETAILED DESCRIPTION OF THE INVENTION

It has been discovered in accordance with the present invention that the reaction of moricizine and hydrochloric acid produces, depending on the reaction conditions, substantially non-hydrated crystalline moricizine hydrochloride and/or hydrated forms of crystalline moricizine hydrochloride. These hydrated forms of crystalline moricizine hydrochloride, containing occluded water within the crystalline lattice structure, are referred to as moricizine hydrochloride hemi-hydrate. While moricizine hydrochloride hemi-hydrate is believed to possess the same utility as non-hydrated moricizine hydrochloride, the hemi-hydrate requires additional processing steps to remove the occluded water impurity. Non-hydrated crystalline moricizine hydrochloride is substantially free of occluded water. The present invention provides reaction conditions for the preparation of moricizine hydrochloride which minimize or eliminate the formation of the undesired moricizine hydrochloride hemi-hydrate.

The moricizine used in the methods of the present invention can be prepared by any of the many procedures known in the art. A representative synthetic procedure is provided by Makharadze et al. (1988) Khim. Farm. Zh. 22: 732. It is preferred, though not necessary, that the moricizine employed be substantially pure.

The moricizine is dissolved in water-miscible organic solvent. Water-miscible solvents according to the present invention are those which exhibit at least partial solubility in water. Representative water-miscible solvents include but are not limited to methanol, ethanol, and n-propanol; absolute ethanol is preferred. The amount of water-miscible solvent employed should be effective to fully dissolve the moricizine in solution at temperatures between from about 20-50° C. In preferred embodiments, moricizine is dissolved in greater than 30 equivalents, and more preferably, greater than 35 equivalents, of absolute ethanol. It may be necessary to use stirring and/or heat to fully dissolve the moricizine.

The solution of moricizine in water-miscible solvent is then contacted with greater than about 1.0 equivalents of hydrogen chloride in the form of hydrochloric acid. In preferred embodiments, about 1.1–1.5 equivalents of hydrogen chloride are added to the moricizine solution, more preferably about 1.2 equivalents. During the addition, the reaction mixture should be maintained at a temperature from about 20° C. to about 50° C. The aqueous acid preferably comprises from about 35 to about 40 weight percent hydrogen chloride, more preferably 36.5 weight percent. In general, the reaction mixture should have a pH of about 1.35–3.0, preferably 1.5–3.0.

After the addition of aqueous acid is complete, the reaction mixture is allowed to cool, typically with stirring. The reaction mixture is then visually monitored for the precipitation of crystalline moricizine hydrochloride. The reaction mixture should be allowed to cool as slowly as possible to effect a correspondingly slow crystallization of moricizine hydrochloride from solution. Preferably, the reaction mixture is allowed to cool under ambient conditions (i.e., about 25° C.) from the temperature maintained during acid addition. The reaction mixture should not be contacted with ice water baths or any other media having a temperature less than about room temperature (i.e., about 25° C.) until crystalline precipitate is observed.

If crystallization is not observed after the reaction mixture has reached room temperature, seeding can be performed by any of the methods known in the art. Preferably, the reaction mixture is seeded with crystalline moricizine hydrochloride.

The amount of water-miscible solvent earlier used to dissolve the moricizine should be selected such that the moricizine hydrochloride can be precipitated from the reaction mixture in the temperature range from slightly greater than room temperature down to about 0° C.

After a precipitate has been observed, the reaction mixture is refrigerated by, for example, immersion in an ice bath to increase the rate of subsequent precipitation. Once precipitation ceases, the resulting crystalline moricizine hydrochloride is separated from its mother liquor and dried by any of the techniques known in the art. To enhance the overall yield of moricizine hydrochloride, the mother liquor can be concentrated and further portions of moricizine hydrochloride recovered therefrom by slowly cooling the concentrate.

Additional objects, advantages, and novel features of this invention will become apparent to those skilled in the art upon examination of the following examples thereof, which are not intended to be limiting.

EXAMPLE 1

To a 250 mL flask equipped with thermometer, condenser, and nitrogen inlet were added 25 grams (0.0585 moles) moricizine and 120 mL (2.048 moles, 35 equivalents) absolute ethanol. The mixture was stirred and heated at 65–80° C. for about 15 minutes, after which time the moricizine was fully dissolved. The heat was turned off and the mixture was allowed to cool with stirring under ambient conditions. When the temperature reached about 35° C., 7.0 grams hydrochloric acid (36.5% HCl, 0.07 moles HCl, 1.2 equivalents HCl) were added. After a precipitate became visible, the mixture was cooled with an ice water bath to about 0° C, maintained at that temperature for about one hour, and then filtered. The solids were dried in a vacuum oven overnight at 50–55° C. to provide 21.98 grams (81% yield) of substantially non-hydrated moricizine hydrochloride. Substantially non-hydrated moricizine hydrochloride was obtained as a white powder having a melt range of 214–217° C., and one strong, sharp peak at about 215° C. on differential scanning calorimetry.

EXAMPLE 2

The procedure of Example 1 was repeated, except that 22 equivalents absolute ethanol were used. The resulting moricizine hydrochloride, containing hydrated moricizine hydrochloride, was a white powder having a melt range of 206–208° C. Differential scanning calorimetry revealed one strong, sharp peak at about 210° C.

EXAMPLE 3

The procedure of Example 1 was repeated, except that the reaction mixture was not allowed to cool at ambient temperature while stirring but was immersed in an ice water bath. The resulting moricizine hydrochloride, containing hydrated moricizine hydrochloride, was a white powder. Differential scanning calorimetry revealed two small, broad peaks at about 88° C. and 210° C.

EXAMPLE 4

The procedure of Example 1 was repeated, except that 0.8 equivalents hydrogen chloride were used. The resulting moricizine hydrochloride, containing hydrated moricizine hydrochloride, was a white powder having a melt range of 200–215° C. Differential scanning calorimetry revealed a medium peak at about 200° C. having a small shoulder at about 217° C.

EXAMPLE 5

The procedure of Example 1 was repeated, except that 26% hydrochloric acid was used. The resulting moricizine hydrochloride, containing hydrated moricizine hydrochloride, was a white powder having a melt range of 200–204° C. Differential scanning calorimetry revealed a medium, broad peak at about 200° C.

Those skilled in the art will appreciate that numerous changes and modifications can be made to the preferred embodiments of the invention and that such changes and modifications can be made without departing from the spirit of the invention. It is therefore intended that the appended claims cover all such equivalent variations as fall within the true spirit and scope of the invention.

What is claimed is:

1. A process for preparing moricizine hydrochloride, comprising the steps of:
    (a) contacting a first solution comprising moricizine end ethanol with hydrochloric acid under reaction conditions effective to form a second solution comprising moricizine hydrochloride; and
    (b) isolating said moricizine hydrochloride from said second solution;
    wherein said process is characterized in that at least one of the following process conditions is present:
    said first solution comprises at least 30 equivalents ethanol per equivalent moricizine; or
    the molar ratio of hydrogen chloride to moricizine is at least 1.1:1.

2. The process of claim 1 wherein said first solution comprises more than about 35 equivalents ethanol per equivalent moricizine.

3. The process of claim 1 wherein said hydrochloric acid comprises about 35 to about 40 weight percent hydrogen chloride.

4. The process of claim 1 wherein said hydrochloric acid comprises about 36.5 weight percent hydrogen chloride.

5. A process for preparing moricizine hydrochloride, comprising the steps of:
    (a) contacting a first solution comprising moricizine and a water-miscible organic solvent with hydrochloric acid under reaction conditions effective to form a second solution comprising moricizine hydrochloride; and (b) isolating said moricizine hydrochloride from said second solution;

wherein said process is characterized in that at least one of the following process conditions is present;

said solution comprises more than 30 equivalents of said organic solvent per equivalent moricizine;

said hydrochloric acid comprises 35 to 40 weight percent hydrogen chloride;

the molar ratio of hydrogen chloride to moricizine is at least 1.1:1; or said isolating step comprises crystallizing said moricizine hydrochloride from said second solution at a rate effective to produce said moricizine hydrochloride substantially non-hydrated form and having a melt range of 214°–217° C., and one strong, sharp peak at about 215° C. on differential scanning colorimetry.

6. The process of claim 1 wherein the molar ratio of hydrogen chloride to moricizine is about 1.2:1.

7. The process of claim 1 wherein said second solution has a pH of about 1.35 to about 3.0.

8. The process of claim 1 wherein said isolating step (b) comprises crystallizing said moricizine hydrochloride from said second solution at a rate effective to produce said moricizine hydrochloride in substantially non-hydrated form substantially free of occluded water and having a melt range of 214°–217° C., and one strong, sharp peak at about 215° C. on differential scanning colorimetry.

9. The process of claim 8 wherein crystallizing said moricizine hydrochloride comprises allowing said second solution to coolant ambient temperature from the temperature maintained during acid addition.

10. The process of claim 8 wherein crystallizing said moricizine hydrochloride comprises cooling said second solution with an external medium having a temperature no less than about 25° C. before precipitation of a visually perceptible amount of moricizine hydrochloride.

11. The process of claim 8 wherein crystallizing said moricizine hydrochloride comprises cooling said second solution with an external medium having a temperature no less than about 25° C. after precipitation of a visually perceptible amount of moricizine hydrochloride.

12. The process of claim 8 wherein crystallizing said moricizine hydrochloride comprises contacting said second solution with at least one seed crystal of moricizine hydrochloride.

13. The process of claim 1 wherein said isolating step (b) comprises filtering said moricizine hydrochloride from said second solution.

14. The process of claim 1 wherein said isolating step (b) comprises drying said moricizine hydrochloride.

15. The process of claim 1 wherein said moricizine hydrochloride isolated in step (b) is substantially crystalline.

* * * * *

UNITED STATES PATENT AND TRADEMARK OFFICE
CERTIFICATE OF CORRECTION

PATENT NO. : 5,202,435
DATED : April 13, 1993
INVENTOR(S) : Gary O. Page

It is certified that error appears in the above-identified patent and that said Letters Patent is hereby corrected as shown below:

Claim 9, Column 6, Line 5: "coolant" should read - - cool at - -.

Signed and Sealed this

Twenty-third Day of August, 1994

Attest:

BRUCE LEHMAN

Attesting Officer     *Commissioner of Patents and Trademarks*